United States Patent [19]
Novotny

[11] 4,273,947
[45] Jun. 16, 1981

[54] HYDROGENATION OF FLUORINE-CONTAINING CARBOXYLIC ACIDS

[75] Inventor: Miroslav Novotny, Denville, N.J.

[73] Assignee: Allied Chemical Corporation, Morris Township, Morris County, N.J.

[21] Appl. No.: 7,875

[22] Filed: Jan. 31, 1979

[51] Int. Cl.$^3$ .................... C07C 31/38; C07C 31/40
[52] U.S. Cl. .................... 568/842; 568/812; 568/814; 568/831; 568/700; 568/838; 568/839; 568/885
[58] Field of Search ............... 568/842, 812, 814, 831, 568/700, 885, 838, 839

[56] References Cited

U.S. PATENT DOCUMENTS

| | | | |
|---|---|---|---|
| 2,862,977 | 12/1958 | Schreyer | 568/842 |
| 3,356,746 | 12/1967 | Anello et al. | 568/842 |
| 3,663,629 | 5/1972 | Fischer et al. | 568/842 |

OTHER PUBLICATIONS

Grimm et al., J. Am. Oil Chemists Soc., 46, No. 2, p. 118, (1968).
Broadbent et al., J. Org. Chem. 24, (1959), pp. 1847–1854.

*Primary Examiner*—Howard T. Mars
*Attorney, Agent, or Firm*—Robert A. Harman; Alan M. Doernberg

[57] ABSTRACT

A process is described for the heterogeneous hydrogenation of fluorine-containing alkyl, cycloalkyl, and benzene carboxylic acids to the corresponding primary alcohols. The hydrogenation can be carried out in the liquid or vapor phase in the presence of a solid rhodium or iridium catalyst, employed as the metal, metallic oxide, or mixture thereof. In the liquid phase, the hydrogenation can be carried out batchwise under mild conditions of temperature and pressure, preferably at about 50°–150° C. and about 5–15 atmospheres, in an atmosphere containing hydrogen gas. A preferred embodiment is the hydrogenation of trifluoroacetic acid in the liquid phase to 2,2,2-trifluoroethanol, said alcohol being useful as an intermediate in the synthesis of the anesthetic, isoflurane, $CF_3CHClOCHF_2$.

7 Claims, No Drawings

HYDROGENATION OF FLUORINE-CONTAINING CARBOXYLIC ACIDS

BACKGROUND AND SUMMARY OF THE INVENTION

This invention relates to a process for hydrogenating a carboxylic acid group in a fluorine-containing alkyl, cycloalkyl or benzene carboxylic acid to the primary alcohol group, in the liquid or vapor phase, in the presence of a solid rhodium or iridium catalyst, employed as the metal, metallic oxide, or mixture thereof.

Fluorine-containing alcohols are useful as solvents for a wide variety of organic compounds and are also useful as reagents for producing fluorine-containing esters of carboxylic acids, in which the alcohol moiety contains fluorine substituents. A commercially important fluorine-containing alcohol is 2,2,2-trifluoroethanol which can be used to produce the known anesthetic, isoflurane, $CF_3CHClOCHF_2$.

Methods for producing fluorine-containing alcohols, such as 2,2,2-trifluoroethanol, usually involve the reduction of esters containing this alcohol moiety. For example, U.S. Pat. Nos. 3,314,987 and 4,072,726 (to Allied Chemical Corporation) describes the hydrogenation of such fluorine-containing esters over a copper oxide-based catalyst to produce fluorine-containing alcohols and similarly, U.S. Pat. No. 3,356,746 (to Allied Chemical Corporation) describes the hydrogenation of fluorine-containing esters over supported and unsupported ruthenium and palladium catalysts.

However, processes for hydrogenating fluorine-containing alkyl carboxylic acids directly to the corresponding primary alcohols are not well known since these acids are generally more resistant to reduction than are the esters. This is particularly true for the lower members of the class such as trifluoroacetic acid and perfluoropropionic acid which are commonly used as solvents for various substrates in hydrogenation processes using platinun catalysts.

U.S. Pat. No. 3,663,629 (1972) describes a process for hydrogenating perfluoroalkane carboxylic acids at elevated temperature and pressure, in the presence of a ruthenium catalyst, thereby producing the corresponding fluorinated 1,1-dihydro alcohols. However, the process requires the presence of an initial aqueous system and is limited to the hydrogenation of $C_4$ and higher perfluorinated alkanoic acids.

The reference, J. Org. Chem. 24, pp. 1847–1854 (1959) describes the hydrogenation of trifluoracetic acid and heptafluorobutyric acid to the corresponding primary alcohols in the presence of a rhenium black formed in situ from the heptoxide. However, the reaction requires, as a minimum, very forcing conditions, including use of a relatively large amount of catalyst calculated as rhenium (viz. 2% by weight), gaseous hydrogen pressures of about 300 atmospheres, temperatures above 200° C. and a reaction time of 18.5 hours.

No mention is made in the above-described references of the use of rhodium or iridium-based catalysts for the heterogeneous hydrogenation of a carboxy group in a fluorine-containing carboxylic acid alkyl, cycloaklyl or benzene to a primary alcohol group.

Since the preparation of fluorine-containing alcohols is potentially most commercially attractive from the direct hydrogenation of the corresponding fluorine-containing carboxylic acids, what is desired is a direct one-step hydrogenation process applicable to a large class of fluorine-containing carboxylic acids proceeding at reasonable rate under mild conditions of temperature and pressure.

SUMMARY OF THE INVENTION

In accordance with this invention, there is provided a process for hydrogenating a carboxy group in fluorine-containing alkyl, cycloalkyl or benzene carboxylic acid to the primary alcohol group comprising the step of contacting said acid in the liquid or vapor phase with an atmosphere containing hydrogen gas in the presence of a supported or unsupported solid rhodium or iridium catalyst, employed as the metal, metallic oxide, or mixture thereof.

A feature of the invention process is the surprising discovery by us of the use of solid supported or unsupported rhodium or iridium catalysts, employed as the metal, or metallic oxide or mixture thereof, such as rhodium on carbon, rhodium on alumina, rhodium oxide hydrate, rhodium black, iridium black, or mixtures thereof, which allow the hydrogenation to be conducted under mild conditions of temperature and pressure.

Advantages of the invention process include the high yield hydrogenation of fluorine-containing $C_2$–$C_3$ alkyl carboxylic acids, particularly trifluoroacetic acid, at low temperature and low pressure, rendering the process extremely attractive from a commercial standpoint.

A further advantage is that said process does not require the initial presence of an aqueous system which may be deleterious to catalytic activity.

By the term "hydrogenation", as used herein, is meant the reduction of a carboxy group in fluorine-containing carboxylic acid to the primary alcohol group wherein hydrogen is the active reducing agent. Also, by the term "contacting" as used herein, is meant the physical interaction of the atmosphere, containing hydrogen gas, with the reaction mixture of fluorine-containing carboxylic acid and solid catalyst.

DETAILED DESCRIPTION OF THE INVENTION AND PREFERRED EMBODIMENTS

The invention process can be represented by the following equation:

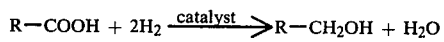

$$R-COOH + 2H_2 \xrightarrow{catalyst} R-CH_2OH + H_2O$$

where R is a fluorine-containing alkyl, cycloalkyl or phenyl group, said alkyl group being linear or branched and said cycloalkyl and phenyl groups being substituted or unsubstituted. By the term "fluorine-containing" is meant that the cycloalkyl or phenyl group contains at least one C-F bond. Said alkyl, cycloalkyl or phenyl groups can also contain substituents including $C_1$–$C_4$ linear or branched alkyl or $C_1$–$C_4$ linear or branched alkoxy substituents, and the like, which are non-interfering under the reaction conditions. As is seen in the above equation, the stoichiometry of the hydrogenation reaction requires at least two moles of elemental hydrogen per mole of fluorine-containing carboxylic acid, thus producing one mole of fluorine-containing primary alcohol.

The scope of fluorine-containing carboxylic acids, applicable in the invention process, having the above formula as defined for R, includes those alkyl, cycloalkyl and benzene carboxylic acids containing at least one C-F bond, 2 to 24 carbon atoms, and at least one carboxy group in the molecule. Representative examples of carboxylic acids applicable in the invention process are monofluoroacetic acid, difluoroacetic acid, 2-phenyl-2,2-difluoroacetic acid, trifluoroacetic acid, 3,3,3-trifluoropropionic acid, perfluoropropionic acid, heptafluorobutyric acid, perfluoroisobutyric acid, perfluorovaleric acid, perfluorohexanoic acid, perfluoroheptanoic acid, perfluorooctanoic acid, perfluorononanoic acid, perfluorodecanoic acid, perfluorocyclohexane carboxylic acid, perfluorocyclohexyl acetic acid, pentafluorobenzoic acid, p-fluorobenzoic acid and 2,4-difluorobenzoic acid.

Preferred carboxylic acids in the invention process are those that are perfluorinated. Also preferred are alkyl carboxylic acids containing 2–10 carbon atoms. More preferred are linear alkyl carboxylic acids containing 2–4 carbon atoms and a particularly preferred acid in the process is trifluoroacetic acid. By the term "acid" as used herein, is meant the fluorine-containing carboxylic acids as described above.

The hydrogenation of a carboxy group in the fluorine-containing acid in the process results in the 1,1-dihydro primary alcohol, illustrated in the above equation in which the carbon to which the primary alcohol group is attached is fluorine free. Other functional groups or radicals contained in the acid may be present which are concomitantly hydrogenated under the reaction process conditions. However, such groups or radicals are not required in the invention process. The term "fluorine-containing" as applied to said alcohol herein, has the same meaning as described above for said acid. Representative examples of fluorine-containing alcohols produced in the invention process are 2-fluoroethanol; 2,2-difluoroethanol; 2-phenyl-2,2-difluoroethanol; 2,2,2-trifluoroethanol; 3,3,3 trifluoro-n-propyl alcohol; 3,3,3,2,2-pentafluoro-n-propyl alcohol; 4,4,4,3,3,2,2-heptafluoro-n-butanol; 2,2-di(trifluoromethyl)-2-fluoroethanol; 5,5,5,4,4,3,3,2,2-nonafluoro-n-pentanol; 6,6,6,5,5,4,4,3,3,2,2-undecafluoro-n-hexanol; 7,7,7,6,6,5,5,4,4,3,3,2,2-tridecafluoro-n-heptanol; 8,8,8,7,7,6,6,5,5,4,4,3,3,2,2-pentadecafluoro-n-octanol; 9,9,9,8,8,7,7,6,6,5,5,4,4,3,3,2,2,-heptadecafluoro-n-nonanol; 10,10,10,9,9,8,8,7,7,6,6,5,5,4,4,3,3,2,2-nonadecafluoro-n-decanol; 1,2,2,3,3,4,4,5,5,6,6-undecafluorocyclohexylmethanol; 2-(1,2,2,3,3,4,4,5,5,6,6-undecafluoro)-cyclohexyl-2,2-difluoroethanol; 1,2,3,4,5-pentafluorobenzyl alcohol; p-fluorobenyl alcohol and 2,4-difluorobenzyl alcohol. A preferred product alcohol in the process is 2,2,2-trifluoroethanol.

The process can be conducted in the liquid or vapor phase. In the liquid phase, the acid can be present in neat form, above its melting point, or dispersed in a liquid or dissolved in a suitable solvent. Such dispersing liquid or solvent, if used, should be inert under the reaction conditions. A solvent if used, should possess adequate solvating ability for the acid, be a non-solvent for the catalyst and provide a solution of the acid below the decomposition temperature of said acid. Representative classes of solvents applicable in the process, include fluorine-containing esters, non-fluorine-containing carboxylic acids, hydrocarbons and water. Preferred class of solvent is fluorine-containing esters including ethyl trifluoroacetate and trifluoroethyl trifluoroacetate. The amount of solvent, if used, can be about 0.1 to 10 parts by weight per part of said acid. However this amount is not critical, lower and higher amounts being also effective with the proviso that sufficient solvent is present to dissolve said acid to initiate and maintain the hydrogenation reaction.

The process can also be conducted in the vapor phase, in which a dispersion of said carboxylic acid at or above its boiling point, in a stream of other vapors or gases including hydrogen gas, is contacted with the catalyst described herein, preferably in a continuous manner.

The novelty in the process is the use of supported or unsupported solid metallic rhodium or iridium, metallic oxides thereof, or mixtures thereof, which allows the hydrogenation of fluorine-containing carboxylic acids to be conducted under mild conditions. The reason why these particular catalysts are surprisingly effective in the hydrogenation of fluorine-containing carboxylic acids is not known. Said catalyst is a solid under the reaction conditions, and can be suspended in the liquid acid, neat or in dispersion or solution during a liquid phase process, or suspended as a fixed or fluidized bed during a continuous vapor phase process. Thus, the solid catalyst acts as a heterogeneous catalyst under the reaction conditions. Representative examples of unsupported catalysts include metallic rhodium, rhodium black, metallic iridium, iridium black, rhodium oxide and iridium oxide. Also included are rhodium and iridium chlorides and rhodium and iridium complexes which decompose under the reaction conditions to the corresponding metals or metallic oxides. By the term "black" is meant a finely divided metal. The catalyst, may also be supported on suitable substrates including carbon, alumina, silica, and other high surface area carriers. Preferred supports are carbon, being activated carbon, and alumina. Representative examples of catalysts supported on various substrates are rhodium on carbon, rhodium on alumina, iridium on carbon, iridium on alumina, rhodium oxide on carbon, rhodium oxide on alumina, iridium oxide on carbon, iridium oxide on alumina, rhodium on silica, rhodium oxide on silica, iridium on silica and iridium oxide on silica. Preferred catalysts are selected from the group consisting of 5 weight percent rhodium on carbon, 5 weight percent rhodium on alumina, rhodium black, iridium black, rhodium oxide hydrate, or mixtures thereof. Particularly preferred catalyst is 5 weight percent rhodium on carbon, also designated herein as 5% Rh/C. The catalysts useful in the invention process may be prepared by conventional methods or obtained commercially.

The amount of total catalyst present in the process, and by the term "total catalyst" is meant active catalyst material including support if present, is not critical for operability and may be from about 0.001 to 20 weight percent of said acid present in either the liquid or vapor phase. A preferred amount is about 5 weight percent total catalyst present of the weight of said acid present, since it has been found by us that the reaction rate is maximized generally at this catalyst concentration. Higher concentrations of catalyst will not significantly increase the rate of the reaction and lower amounts will still be operable for obtaining high yields, but the reaction rate will be proportionally slower.

The process in the liquid phase may be conducted as a simple batch reaction, or as a series of batch reactions in a continuous manner, in which the liquid product mixture is removed from the reaction vessel, such as by decantation or distillation under vacuum, and a fresh charge of said acid added to the reactor to repeat the reaction process. In general, the original catalyst may be utilized in this manner for about an additional 3 to 5 batch reactions before its catalytic activity becomes inappreciable.

The process in the vapor phase, can be conducted, preferably in a continuous manner, by contacting a stream of acid, above its boiling point, and hydrogen gas with the solid catalyst described herein, as a fixed or fluidized bed.

For effective hydrogenation in the liquid phase, the catalyst should be suspended throughout the liquid acid media during the hydrogenation to insure maximum contact of catalyst surface with the acid. This is generally accomplished by agitation, or continuous stirring of the reaction contents during the process.

Water is formed in the reaction mixture as a by-product during the hydrogenation as shown in the above equation. However, the presence of water initially in the process is not required or even desired, since we believe that water can compete with the acid for active sites on the catalyst surface, thus decreasing the rate of hydrogenation.

The temperature in the liquid or vapor phase process must be below the decomposition or decarboxylation temperature of the acid being hydrogenated. In the liquid phase process, the temperature must also be at about, or below, the boiling point of said acid, and above the melting point of said acid, under the reaction conditions, such that a substantial amount of acid is present as a liquid. The process temperature range includes the range of about 50°–200° C., and preferably about 50°–150° C. Temperature range in the vapor phase embodiment is generally above the boiling point of said acid.

Pressure in the process may be from 1 to 500 atmospheres. Higher pressures than 500 atmospheres, being the upper safety limit of known commercial pressure apparatus, may also be used, as well as lower pressures than one atmosphere provided sufficient hydrogen gas is present to initiate and maintain the hydrogenation reaction. From a commercial standpoint, milder conditions are very desirable and for this reason, pressures of about 5 to about 15 atmospheres are preferred in the process reaction. In some instances, higher pressures are not beneficial. For example, pressures above 11.6 atmospheres, do not significantly increase the reaction rate during the hydrogenation of trifluoroacetic acid, at 73° C., in the presence of 5% rhodium on carbon catalyst, and said acid being in the liquid or vapor phase.

The atmosphere with which the acid, being in the liquid or vapor phase, is in contact during the process contains hydrogen gas. Other inert gases such as argon, nitrogen, may also be present in said atmosphere as long as sufficient hydrogen gas is present to initiate and maintain the hydrogenation reaction. This amount is generally about 2 moles of hydrogen gas per mole of acid desired to be hydrogenated. Usually a slight excess of about 20 mole percent of hydrogen gas above the stoichiometric quantity is utilized to insure high yields in the process. Preferably, the atmosphere contacting the acid during the process consists essentially of hydrogen gas.

Yields of fluorine-containing alcohol in the process, based on the starting amount of fluorine-containing carboxylic acid, are as high as 90% of theory and in the preferred embodiments are about 94% of theory and higher.

Length of time for conducting the process either in the liquid or vapor phase will depend upon the particular acid, catalyst, temperature, pressure employed, and the like. In general, reaction times of about 2–24 hours will produce satisfactory yields of product alcohol in the liquid phase process. Contact times of about 1 to 10 seconds will produce satisfactory yields of product alcohol in a continuous vapor phase process. In the preferred embodiment, where trifluoroacetic acid is hydrogenated in the liquid phase, in the presence of 5% rhodium on carbon, at a temperature of about 50°–150° C. and a pressure of about 5–15 atmospheres, in an atmosphere consisting essentially of hydrogen gas, reaction times of about 2–6 hours will generally produce product 2,2,2-trifluoroethanol in yields of about 90–95% of theory.

In some instances, an induction period will be observed in the initial stage of the process i.e. no observed pressure drop in the hydrogen atmosphere. The reason for this is not well understood. This induction period has been observed by us when utilizing rhodium on alumina and iridium black as catalysts and higher perfluorinated acids than trifluoroacetic acid, such as perfluoropropionic and perfluorobutyric acids. However, this observed induction period is not deleterious to the overall yield of product alcohol, but merely requires proportionately longer reaction time periods.

The product alcohol can be isolated from the reaction mixture obtained in either the liquid or vapor phase process by conventional methods such as fractional distillation, column and gas chromatography and the like. Purification of the obtained alcohol can also be accomplished by the above-described conventional methods and the like. Methods for isolating and purifying the product alcohol will be obvious to one skilled in the art.

Apparatus for carrying out the invention process in the liquid phase can be any conventional type of glass or steel pressure reactor apparatus equipped with means for heating and stirring the reaction contents during the reaction, means for observing and monitoring the reaction pressure, means for introducing the reactants and means for recovering products and spent catalyst. Apparatus for carrying out the process in the vapor phase in a continuous manner can be any conventional continuous fixed bed or fluidized bed apparatus with means for mixing a stream of vaporized acid and hydrogen gas and contacting the composite stream with the catalyst described herein for a predetermined contact time interval. Apparatus for conducting the invention process will be obvious to one skilled in the art from this disclosure.

It is preferred during the liquid phase process to initially charge the catalyst and acid to the reactor and degasify the mixture, for example, such as by first freezing the mixture and then subjecting the contents to a vacuum to remove gases in the liquid acid and absorbed gases off from the surface of the catalyst. The mixture is then allowed to thaw to liquify, hydrogen gas introduced and the reaction carried out. Other techniques for activating the catalyst surface can also be used and will be obvious to one skilled in the art. The progress of the reaction process can be monitored by a conventional pressure gauge or manometer and the process is continued until no further pressure drop occurs in which a steady state hydrogen concentration prevails.

A preferred embodiment of the invention process is where the acid is trifluoroacetic acid, in the liquid phase, said catalyst is 5 weight percent rhodium on carbon, total catalyst is present in an amount of about 1-10 weight percent and more preferably 5 weight percent, of said acid present, said temperature is about 50°-150° C., and said pressure is about 5-15 atmospheres, said atmosphere consisting essentially of hydrogen gas, and said resulting alcohol being 2,2,2-trifluoroethanol.

The following examples are illustrative of the best mode of carrying out the invention as contemplated by us and should not be construed to be limitations on the scope or spirit of the instant invention.

DESCRIPTION OF THE PROCEDURE USED IN EXAMPLES

The following hydrogenation runs were carried out in a thick wall glass reactor attached to a metal pressure line. The line was equipped with a pressure gauge to read from 0–300 psig and connected through a manifold to sources of hydrogen, nitrogen and a vacuum pump. The volume of the whole system, including the reactor, was 0.206 liter. The contents of the reactor were stirred with a magnetic stirrer. Highest purity trifluoroacetic acid, commercially obtained, redistilled and iron free, and commercially available catalysts, were used in all runs. The runs were begun by charging the acid and catalyst into the reactor, degasifying the reaction mixture (one freeze-evacuate-thaw cycle) and then admitting hydrogen gas to a desired initial reaction pressure. After testing for leaks, the reactor was immersed in a constant temperature oil bath maintained at a desired constant temperature. The course of the reaction was followed by use of a pressure gauge in which the observed pressure drop resulting from the uptake of hydrogen was monitored throughout the process. The resulting liquid product mixture was analyzed by gas chromatography employing pentafluorobenzene as an internal standard. The results of the runs were reproducible in subsequent runs utilizing the same conditions. No reaction occurred in any of the runs in the absence of catalyst.

EXAMPLE 1

The above-described reactor was charged with 0.1 grams of 5% rhodium on carbon catalyst and 2.05 grams (17.6 mmols) of trifluoroacetic acid. The reactor contents were degasified by the procedure described above, and the reactor pressurized with 160 psig of hydrogen gas. The reactor was immersed into an oil bath maintained at 100° C. and the liquid reactor contents were stirred for 6 hours. The reaction pressure was monitored during the course of the reaction in which a steadily decreasing reaction pressure with time was noted. At the end of the reaction, as evidenced by a steady state reaction pressure, the liquid product mixture was distilled out of the reactor by means of a vacuum line and qualitatively and quantitatively analyzed by gas chromatography. Results showed only a small amount of acid remaining in the mixture and product 2,2,2-trifluoroethanol obtained in a 94% yield of theory.

EXAMPLE 2

Utilizing the apparatus and general procedure described in Example 1, 3.31 grams of fresh acid were added to the same catalyst used in Example 1, in a recycle of the catalyst. The reactor contents were heated at 150° C. for 5 hours under stirring. Analysis of the liquid product mixture by gas chromatography showed the presence of 85.6 weight percent 2,2,2-trifluoroethanol in the mixture corresponding to a yield of about 96% of theory.

EXAMPLE 3

Utilizing the apparatus and general procedure described in Example 1, the same quantities of materials were used, but the reaction was conducted at 50° C. for six hours under stirring. Analysis of the liquid product mixture by gas chromatography showed product 2,2,2-trifluoroethanol obtained in a 94% yield of theory.

EXAMPLE 4

The influence of the bulk concentration of trifluoroacetic acid in the reaction mixture on the initial reaction rate was studied utilizing the apparatus and general procedure described in Example 1, with the following modifications. The catalyst amount was 2.5 weight percent of the acid. The pressure was 11.5 atmospheres of hydrogen gas and a series of runs was conducted at 54° C., 67° C., 72° C., 82° C. and 98° C. each for 3 hours. The concentration of 2,2,2-trifluoroethanol was calculated at 10, 15, 20, 25, 30, 35, 40 and 45 minute intervals in the runs from the observed pressure drops and the stoichiometric equation:

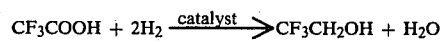

$$CF_3COOH + 2H_2 \xrightarrow{catalyst} CF_3CH_2OH + H_2O$$

A plot of these calculated concentration values versus corresponding time periods yielded straight lines in each case up to about 30% conversion of the acid. The initial rate of hydrogenation is therefore believed to be independent of the bulk concentration of trifluoroacetic acid and therefore believed to be zero order with respect to the acid. At higher conversions, a decline in the hydrogenation rate was observed. We believe that this is due to an inhibiting effect upon the catalyst surface due to the competitive surface absorption of the products, water and 2,2,2-trifluoroethanol.

EXAMPLE 5

The influence of catalyst concentration on the initial reaction rate was studied. Utilizing the apparatus and general procedure described in Example 1, with the following modifications, a series of 5 runs was made at 73° C. under 11.5 atmospheres of hydrogen gas for a period of 3 hours each, using 1.9 grams of trifluoroacetic acid using various concentrations of 5% rhodium on carbon catalyst. The resulting initial reaction rates, given by the symbol, $r_o$, as a function of the catalyst concentration, expressed as a weight percentage of the reaction mixture, are listed below in Table I.

TABLE I

| Weight % of catalyst[a] | 0.7 | 1.7 | 2.7 | 4.2 | 5.5 |
|---|---|---|---|---|---|
| $r_o \times 10^6 \frac{moles}{sec}$ | 0.2 | 1.3 | 3.0 | 5.2 | 5.7 |

[a]Defined as $\frac{wt.\ of\ catalyst}{wt.\ of\ reaction\ mixture} \times 100$.

As is seen, the initial rate, $r_0$, increases up to about 5 weight percent catalyst concentration. Catalyst concentrations above this value did not significantly increase the reaction rate.

EXAMPLE 6

The influence of the hydrogen pressure upon the initial reaction rate was studied. A series of 5 runs, utilizing the apparatus and general procedure described in Example 1, was conducted except that the runs were made at 73° C., a 2.5 weight percent catalyst (5% rhodium on carbon) concentration was used and 1.95 grams of trifluoroacetic acid was the initial acid charge. Each run was conducted for 3 hours at varying pressures of hydrogen gas. The results are listed in Table II below.

TABLE II

| $P_o[atm]^a$ | 6.1 | 6.9 | 8.6 | 10.2 | 11.6 |
|---|---|---|---|---|---|
| $r_0 \times 10^6 \frac{moles}{sec}$ | 1.6 | 1.8 | 2.2 | 2.4 | 2.7 |

$^aP_o$ = pressure in atmospheres of hydrogen gas

As is seen, the initial reaction rate increases as the pressure increases. A plot of ln $r_0$ versus ln $P_0$ gave a straight line with a slope equal to +0.81 and an ordinate intercept of −14.79. Consequently the initial rate in the studied pressure range (6–12 atmospheres) under these conditions can be expressed as:

$$r_o = 3.8 \times 10^{-7} P_o 0.81 (moles/sec)$$

EXAMPLE 7

The influence of temperature upon the reaction rate constant, designated by the symbol $k_O$, was studied. A series of 6 runs was carried out at various temperatures, t, between 59° C. and 114° C. at a 2.5 weight percent catalyst (5% rhodium on carbon) concentration and a pressure of hydrogen gas at 11.5 atmospheres, utilizing the apparatus and general procedure as described in Example 1. The results are listed below in Table III.

TABLE III

| t[°C.] | 59 | 67 | 72 | 82 | 98 | 114 |
|---|---|---|---|---|---|---|
| $k_0 \times 10^5 \frac{moles}{sec \times gm\ cat}$ | 3.2 | 4.5 | 5.3 | 7.0 | 8.3 | 8.4 |

As is seen, the reaction rate constant increases with increasing temperature up to about 114° C. At temperatures above this, no further significant increase in the rate constant is observed. A standard Arrhenius plot using the above data yielded an apparent activation energy for the reaction under the above-described conditions of about 8.2 kcal/mole.

EXAMPLE 8

A series of runs was made utilizing different catalysts in the process and noting the resulting effect on the reaction rate constant, $k_0$. Utilizing the apparatus and general procedure described in Example 1, trifluoroacetic acid, 1.9 grams, was reacted with hydrogen gas under a pressure of 11.2 atmospheres of hydrogen, at 113° C., in the presence of the following catalysts and their amounts, listed below in Table IV.

TABLE IV

| Catalyst | $k_0 \times 10^5 \frac{moles}{sec \times gm\ cat}$ |
|---|---|
| 0.1 gm of 5% Rh/C | 7.6 |
| 0.1 gm of 5% Rh/Al$_2$O$_3$$^a$ | 0.7 |
| 0.05 gm of Rh black | 3.1 |
| 0.05 gm of Ir black$^b$ | 7.6 |

TABLE IV-continued

| Catalyst | $k_0 \times 10^5 \frac{moles}{sec \times gm\ cat}$ |
|---|---|
| 0.05 gm of Rh$_2$O$_3$ . 5H$_2$O | 9.5 |

$^a$About a 10 minute induction period.
$^b$About a 22 minute induction period.

An induction period prior to hydrogenation was noted in some cases as indicated above.

EXAMPLE 9

Higher perfluoroalkanoic acids than trifluoroacetic acid were also successfully hydrogenated in the invention process. Utilizing the apparatus and general procedure described in Example 1 and 0.05 gram of 5% rhodium on carbon, 1.95 grams of the corresponding acid were reacted at 98° C., under a pressure of 11.5 atmospheres of hydrogen gas at a period of 3 hours. The resulting calculated reaction rate constants are tabulated below in Table V.

TABLE V

| Acid | $k_0 \times 10^5 \frac{moles}{(sec \times gm\ cat)}$ |
|---|---|
| CF$_3$COOH | 8.3 |
| CF$_3$CF$_2$COOH$^a$ | 0.4 |
| CF$_3$CF$_2$CF$_2$COOH$^b$ | 0.2 |

$^a$About a 20 minute induction period.
$^b$About a 30 minute induction period.

EXAMPLE 10

A continuous vapor-phase hydrogenation of trifluoroacetic acid was carried out by passing a gaseous mixture of hydrogen and trifluoroacetic acid, in a molar ratio of about 10:1, over a 5% Rh on carbon catalyst, at atmospheric pressure, at 125° C., for a constant time of about 3 seconds. The contacting was performed in a glass microreactor of about 2 ml. volume. Gas chromatographic analysis of the product mixture showed that about 1.4 molar percent of trifluoroacetic acid was converted to 2,2,2-trifluoroethanol. We believe that substantially higher conversions can be achieved utilizing higher pressures, temperatures and contact times.

I claim:

1. A process for hydrogenating the carboxy group in 2,2,2-trifluoroacetic acid to the primary alcohol group comprising the step of contacting said acid in the liquid phase with an atmosphere containing hydrogen gas in the presence of a supported or unsupported solid rhodium or iridium catalyst, employed as the metal, metallic oxide, or mixture thereof; at temperature of about 50°–150° C. and pressure of about 5–15 atmospheres.

2. The process of claim 1 wherein said catalyst is unsupported.

3. The process of claim 1 wherein said catalyst is supported on carbon or alumina.

4. The process of claim 1 wherein said catalyst is selected from the group consisting of 5 weight percent rhodium on carbon, 5 weight percent rhodium on alumina, rhodium black, iridium black, rhodium oxide hydrate, or mixtures thereof.

5. The process of claim 1 wherein said catalyst, in supported or unsupported form, is present in an amount of about 0.001 to 20 weight percent of said acid.

6. The process of claim 4 wherein said catalyst is 5 weight percent rhodium on carbon.

7. The process of claim 6 wherein said catalyst is present in an amount of about 1–10 weight percent of said acid present and said atmosphere consists essentially of hydrogen gas.

* * * * *